(12) United States Patent
Fuller

(10) Patent No.: US 11,369,519 B2
(45) Date of Patent: Jun. 28, 2022

(54) MASK FOR TREATING DRY EYES

(71) Applicant: LABORATOIRES THEA, Clermont-Ferrand (FR)

(72) Inventor: Edmund Thomas Fuller, Christchurch (NZ)

(73) Assignee: LABORATOIRES THEA, Clermont-Ferrand (FR)

(*) Notice: Subject to any disclaimer, the term of this patent is extended or adjusted under 35 U.S.C. 154(b) by 531 days.

(21) Appl. No.: 16/461,711

(22) PCT Filed: Nov. 10, 2017

(86) PCT No.: PCT/EP2017/078956
§ 371 (c)(1),
(2) Date: May 16, 2019

(87) PCT Pub. No.: WO2018/091380
PCT Pub. Date: May 24, 2018

(65) Prior Publication Data
US 2019/0358087 A1 Nov. 28, 2019

(30) Foreign Application Priority Data
Nov. 17, 2016 (FR) ........................ 1661145

(51) Int. Cl.
*A61F 9/04* (2006.01)
*A61F 7/00* (2006.01)

(52) U.S. Cl.
CPC .............. *A61F 9/04* (2013.01); *A61F 7/007* (2013.01); *A61F 2007/0004* (2013.01);
(Continued)

(58) Field of Classification Search
CPC ...... A61F 2007/0004; A61F 2007/0059; A61F 2007/0062; A61F 2007/0071;
(Continued)

(56) References Cited

U.S. PATENT DOCUMENTS 6,823,860 B2   11/2004   Igaki et al.
9,949,872 B2    4/2018   Fuller
(Continued)

FOREIGN PATENT DOCUMENTS

CN    103156766 A    6/2013
EP      1393699 A1   3/2004
(Continued)

OTHER PUBLICATIONS

English (Machine) Translation of JP2013123534A, Jun. 24, 2013, 10 pages (translation retrieved from Google Patents) (Year: 2013).*
(Continued)

*Primary Examiner* — Kaitlyn E Smith
*Assistant Examiner* — Bradford C. Blaise
(74) *Attorney, Agent, or Firm* — Nixon & Vanderhye

(57) ABSTRACT

Disclosed is an eye mask adapted to cover the eyes and the eyelids of a user. The mask includes a main body including an electrical heater and a battery configured to supply the electrical heater and a removable member removably linked to the main body. The removable member includes a wall forming a reservoir provided with retaining orifices adapted to retain a liquid, in particular water, under the effect of the surface tension between the liquid and walls of the orifices. Also disclosed is a method of using such a mask.

17 Claims, 3 Drawing Sheets

(52) U.S. Cl.
CPC ............... *A61F 2007/0062* (2013.01); *A61F 2007/0078* (2013.01); *A61F 2007/0094* (2013.01); *A61F 2007/0095* (2013.01)

(58) Field of Classification Search
CPC ...... A61F 2007/0078; A61F 2007/0088; A61F 2007/0094; A61F 2007/0095; A61F 2007/0277; A61F 7/007; A61F 9/04
See application file for complete search history.

(56) References Cited

U.S. PATENT DOCUMENTS

| | | | |
|---|---|---|---|
| 2003/0056281 A1 | 3/2003 | Hasegawa | |
| 2004/0237969 A1* | 12/2004 | Fuller | A61H 35/02 |
| | | | 128/858 |
| 2014/0336565 A1* | 11/2014 | Nichols | A61M 11/042 |
| | | | 604/24 |
| 2014/0364927 A1* | 12/2014 | Fuller | A61F 7/00 |
| | | | 607/104 |
| 2017/0266035 A1* | 9/2017 | Kuo | H05B 1/0272 |

FOREIGN PATENT DOCUMENTS

| | | | | |
|---|---|---|---|---|
| EP | 2961363 A1 | | 1/2016 | |
| JP | 2013123534 | * | 6/2013 | ............ A61H 33/12 |
| JP | 2015-216974 A | | 12/2015 | |
| WO | 2012/114066 A1 | | 8/2012 | |
| WO | 2016/176175 A1 | | 11/2016 | |

OTHER PUBLICATIONS

International Search Report and Written Opinion, dated Feb. 12, 2018, from corresponding PCT application No. PCT/EP2017/078956.

* cited by examiner

MASK FOR TREATING DRY EYES

BACKGROUND OF THE INVENTION

Field of the Invention

The present invention concerns an eye mask, configured to cover the eyes and the eyelids of a user, for acting against dryness of the eyes by improving the quality of the tear film covering the cornea of the eye.

The tear film present on the cornea of the eye comprises several successive layers including a layer referred to as aqueous and a lipid or oily layer constituted by complex lipids (meibum) secreted by the glands situated on the edge of the eyelids, the meibomian glands.

The lipid layer constitutes the outermost layer of the tear film and prevents rapid evaporation of the water contained in the tears. Dysfunction of the meibomian glands may result in thicker secretions than normal which block the glands, so preventing the release of those secretions into the tear film.

This causes a sensation of dryness of the eye, of the presence of a foreign body ("grain of sand" sensation), inflammation of the eyelids, swelling of the glands, and/or disturbed vision.

Unblocking of the meibomian glands may be obtained under the effect of heat, the lipid secretions being rendered fluid and liquid under the effect of the heat. An optimal result is attained under the effect of hot air (at approximately 50° C.) saturated with water vapour. A sufficient duration is moreover required, of the order of ten minutes, in saturated hot air, to obtain a good result.

Description of the Related Art

Document EP2961363 presents a therapeutic device of the eye mask type comprising a phase-change material making it possible to maintain a sufficient temperature for the device for the duration of the treatment, and a water reservoir.

However, such a device presents a certain number of constraints for use. It must be heated in advance of its use in order to liquefy the phase-change material, which may take a long time and consume a large amount of energy. Furthermore, the control of the temperature throughout the application of the mask is imperfect. The water that is carried must also be heated, and the energy necessary for its heating may be great. Furthermore, the filling of the device with water, which employs porous members, could be simplified. Lastly, such a device is obscuring, and does not enable the user to see during its application.

SUMMARY OF THE INVENTION

The present invention is directed to solving at least one of the aforesaid drawbacks.

Thus, the invention relates to an eye mask adapted to cover the eyes and the eyelids of a user. The mask comprises a main body comprising electrical heating means and a battery configured to supply the electrical heating means, and a removable member removably linked to the main body. The removable member comprises a wall forming a reservoir provided with retaining orifices adapted to retain a liquid, in particular water, under the effect of the surface tension between said liquid and walls of the orifices. The wall forming a reservoir is advantageously configured to surround the eyes of a user wearing said mask.

The mask provided in the invention thus enables the treatment of dry eyes by decongestion of the meibomian glands, in an easy and autonomous manner. The use of a battery enables the heating and/or maintenance of the temperature of the air present in a mask, in particular during the wearing of the mask by a user, without the mask being linked to an external source of energy. The removable member forming a reservoir by holding water under the effect of surface tension makes it possible, after easy filling, to carry in the mask a sufficient quantity of water (or other liquid or solution) to saturate the air present in the mask with vapour for the duration of application. The particular configuration of the reservoir for liquid (generally water) employing orifices retaining the water under the effect of the surface tension between the water and the wall of those orifices enables precise control of the quantity of water carried in the mask at the start of application. The configuration of the wall forming a reservoir provides good distribution of the store of liquid (generally water) around the eyes of the user, and enables uniformly saturated air to be obtained in the mask. It also increases the clearance in front of the user's eyes, allowing the user to blink when he uses the masks.

The removable member may comprise a first part comprising the wall forming a reservoir, and a second part providing air-tightness with the face of a user wearing said mask.

The first part and the second part may be constituted by distinct pieces, the first part being constituted of a material that is plastic, and the second part being formed of a material that is elastic.

The removable member or part is advantageously air-tight with respect to an inside wall of the main body, so as to form a volume in front of the user's eyes that is sealed to the air.

The second part of the removable member may furthermore provide air-tightness with respect to an inside wall of the main body.

In an embodiment of the mask, the retaining orifices are configured in terms of size and number to retain between 0.5 g and 1.5 g of water, and preferably between 0.7 g and 1 g of water.

In a mask according to a preferred variant of the invention, when the removable member is linked to the main body, the wall forming a reservoir is in contact with an inside surface of the main body, the heating means being configured so as to heat said inside surface.

The removable member may be linked to the main body by the matching of shape between the inside surface of the main body and an outside surface of the wall forming a reservoir.

A mask in accordance with an embodiment of the invention may comprise at least one temperature sensor and at least one means for regulating the supply of the heating means by the battery, the temperature sensor and the regulating means being linked.

The invention also relates to a set comprising a mask as described earlier and a base adapted to receive the main body of said mask and supply it with electricity to recharge the battery thereof.

Such a set may be configured such that the electricity supply of said main body furthermore enables the heating of the heating means without them being supplied by the battery, when said main body is received on the base.

The base may comprise a hollow for receiving the main body of the mask, said hollow having a shape preventing the main body of the mask from being received on said base when the removable member is linked to said main body.

The base may comprise a housing configured to receive the removable member.

The set may further comprise a receptacle adapted to receive the removable member for the filling of said wall forming a reservoir, the base further comprising a means for receiving the receptacle when said receptacle is empty.

The main body of the mask or the base may comprise wired or wireless communication means adapted to communicate with a remote system.

Lastly, the invention relates to a method of using a mask as described above, the method comprising:
- filling with liquid the orifices of the wall forming a reservoir;
- linking the removable member to the main body;
- supplying the heating means by the battery;
- regulating the supply of the heating means for the whole or part of a so-called time of application, in order to maintain the air contained in an internal space of the mask within a predefined temperature range for the whole or part of the time of application.

Still other particularities and advantages of the invention will appear in the following description.

BRIEF DESCRIPTION OF THE DRAWINGS

In the accompanying drawings, given by way of non-limiting example.

DESCRIPTION OF THE PREFERRED EMBODIMENTS

Figure 1:
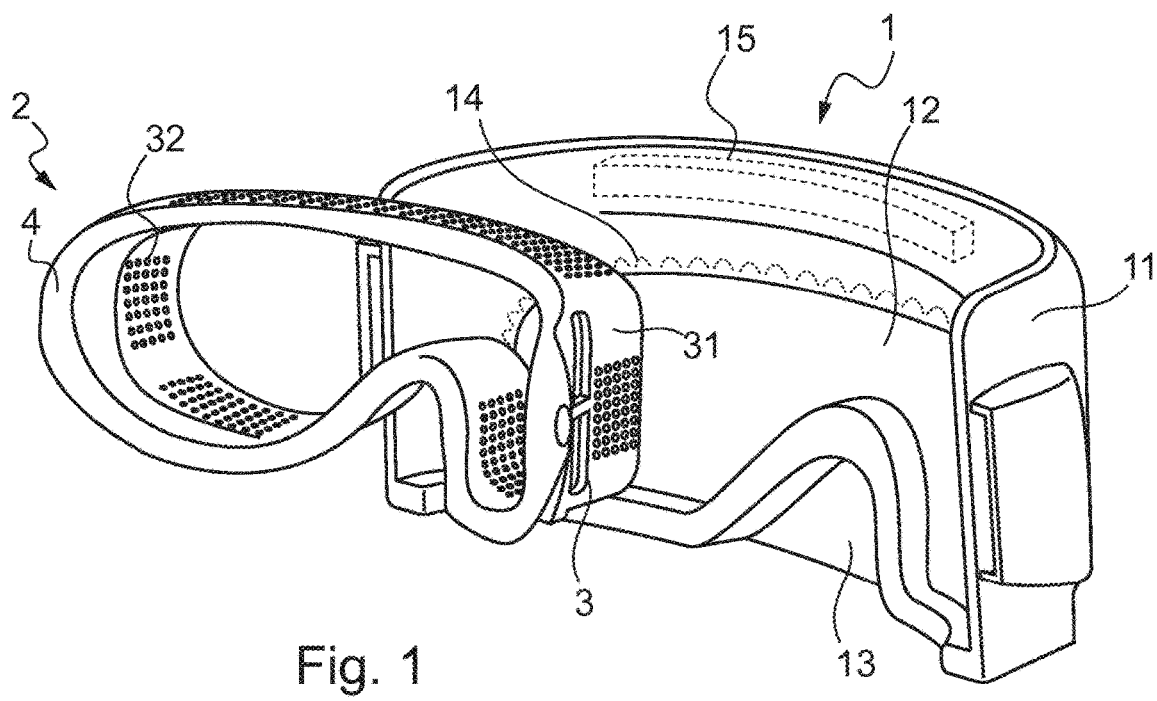
FIG. 1 presents a mask in accordance with an embodiment, in a diagrammatic view in three dimensions.

FIG. 1 presents a mask in accordance with an embodiment of the invention. The mask comprises a main body 1. As it is an eye mask, the main body 1 has a general shape adapted to conform to the shape of and to cover the facial zone comprising the eyes of a wearer. The main body may thus comprise a frame 11 surrounding a front zone 12. The frontal zone may be transparent. It may for example be formed from polycarbonate or from glass, so as to enable the user of the mask to see during its application. The frame 11 may for example have a lower cut-out 13 for the passage of the user's nose. The main body forms an inside volume, corresponding to the inside volume of the mask, in which obtaining air saturated with vapour of a liquid (typically water) is sought during the use of the mask, that is to say during a period of application.

The main body comprises electrical heating means 14, typically comprising resistors, which may be powered by a battery 15 which the main body comprises. The battery can in particular be disposed in the upper zone of the frame 11. As the heating means 14 and the battery 15 are inside the main body, they are diagrammatically represented in dashed line in FIG. 1 in the interest of the proper understanding of the invention.

The battery is advantageously removable in relation to the main body 1, in order to be able to be replaced if need be by a charged battery or a new battery for example in case of malfunction. It may for example be accessible via a trap door provided on the surface of the main body 1.

The heating means 14 are advantageously distributed on the periphery of an inside surface of the main body 1. In order to enable them to be heated with sufficient energy to vaporize a quantity of water enabling the air included in the mask to be saturated for a sufficient time (for example of the order of 10 minutes), rechargeable lithium batteries are advantageously employed.

The main body may also comprise at least one temperature sensor making it possible to measure the temperature of the air inside the mask. The temperature sensor or sensors are linked to the heating means, via a programmable temperature regulation system, in order to enable the regulation of the temperature during the treatment.

The main body 1 may also bear means enabling the mask to be held in position during its use. An elastic strap may be successfully employed for such purpose. The elastic strap is dimensioned to pass around the user's head when the mask is used.

The mask also comprises a removable member 2. The removable member 2 may be attached to the main body 1 or be separated from it. In the embodiment represented here, the removable member has a dual function of sealing and as a reservoir of liquid.

More specifically, in the represented example, the removable member 2 comprises a first part 3 having the function of a reservoir, and a second part 4 providing the sealing function or functions. The first part 3 and the second part 4 may be constituted by distinct pieces, linked together. In particular, the second part 4 may be moulded onto the first part 3.

Figure 2:
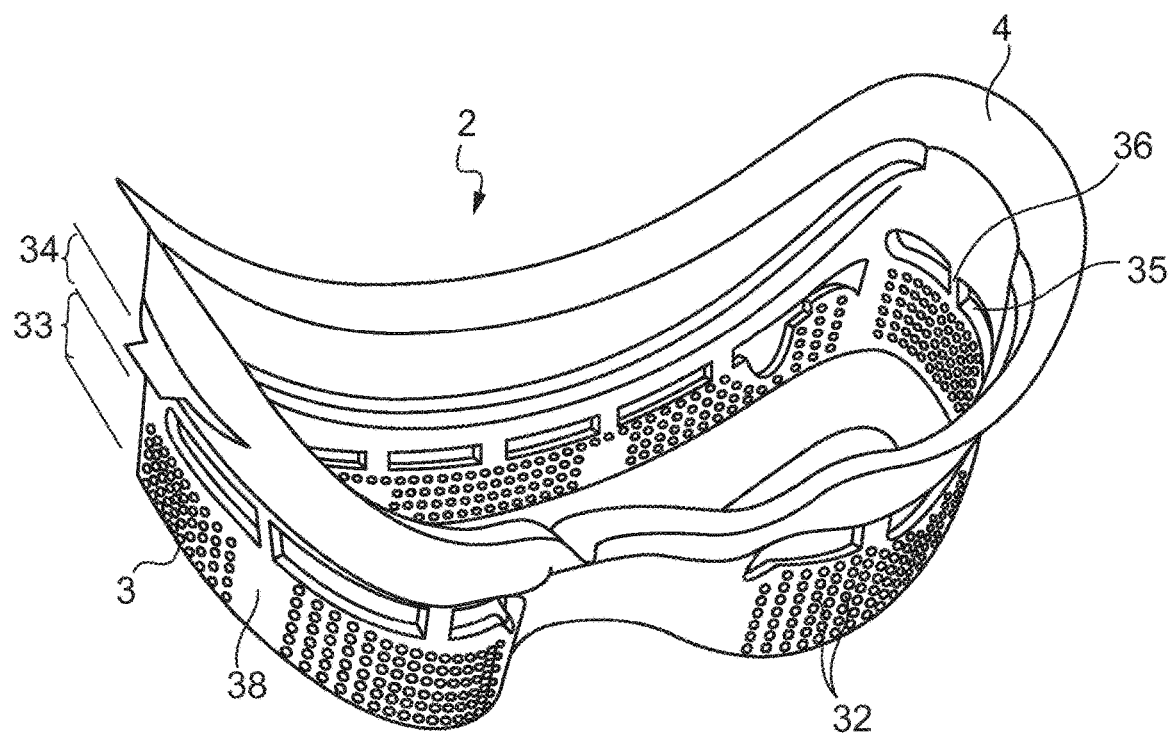
FIG. 2 presents a detailed view of the removable member of the mask of FIG. 1, in a first diagrammatic view in three dimensions.
Figure 3:
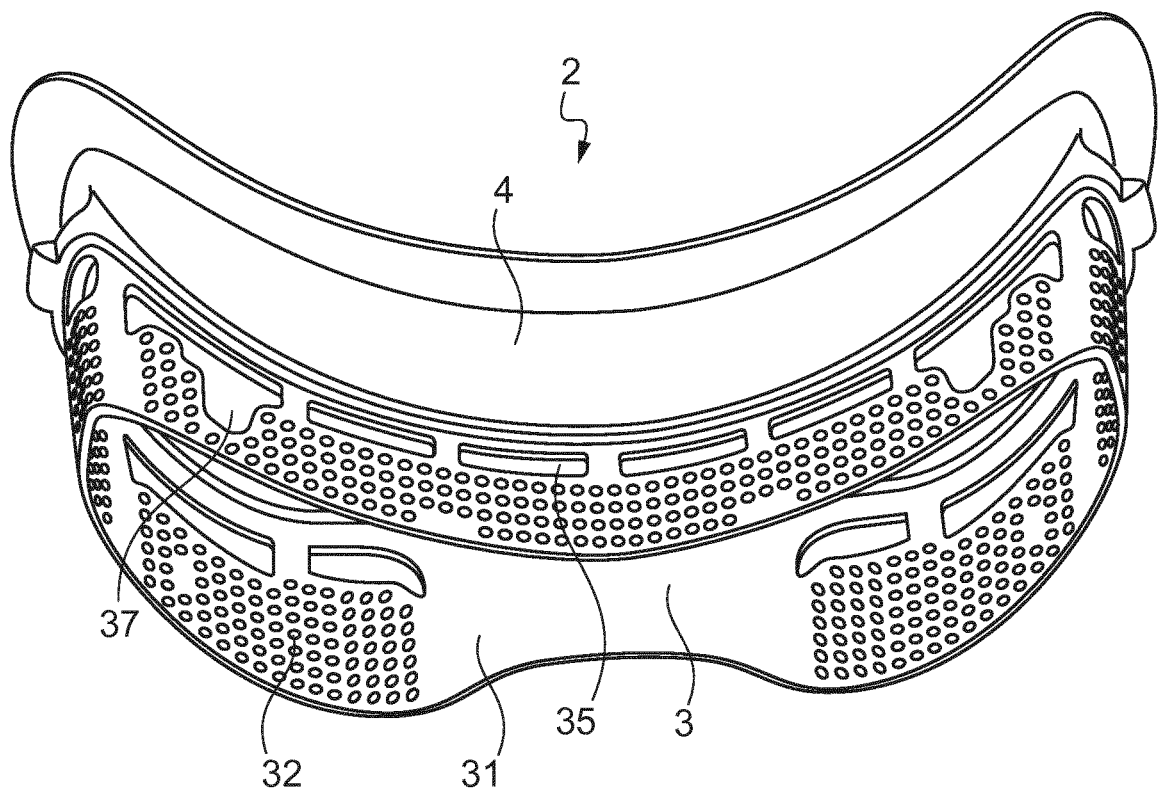
FIG. 3 presents a detailed view of the removable member of the mask of FIG. 1, in a second diagrammatic view in three dimensions.

The reservoir function is provided by a wall 31 of the removable member 2. The wall 31 is provided with apertures 32. The apertures 32 are, in the represented embodiment, through-holes which extend through the wall 31. These orifices may have various shapes. Nevertheless, round holes (forming orifices 32 in the wall 31 that have the shape of a cylindrical solid of revolution) may advantageously be employed, as represented in FIGS. 2 and 3 in particular. Such orifices may easily be obtained in the context of production at industrial scale, in particular by direct moulding or by boring. Furthermore, round holes are easy to clean. Lastly, they limit the loss in rigidity of the member in which they are bored (compared with holes of other geometries).

The orifices 32 are dimensioned so as to enable water to easily penetrate therein when the removable member 2 or at least the first part 3 of the removable member 2 comprising the orifices 32 is immersed, while enabling the water (or other liquid) to be retained under the effect of the surface tension created with the walls of the orifices 32, when the removable member is emerged. In the case of round holes, the diameter of the orifices 32 may be comprised between 1.00 and 1.50 mm, it being possible for example for the orifices all to have an average diameter of 1.30 mm.

Moreover, the number of orifices is adapted such that the reservoir comprises sufficient liquid (generally water) to ensure the presence of air saturated with vapour of that liquid in the mask for the whole time of application predefined for the mask, without however the quantity of liquid being excessive which would render the evaporation difficult and highly energy-consuming, such that it would be complex to equip the mask with a battery of sufficient capacity.

Thus, the size and number of the water retaining orifices may for example be configured to retain between 0.3 g and 2.5 g of water and preferably between 0.5 g and 1.5 g of water, and still more preferably between 0.7 g and 1 g water (or of another liquid having identical or analogous physical properties, in particular as regards its mass and the forces of surface tension created in relation to walls of the orifices).

The quantity of water to retain of course depends on the quantity of air held within the mask during its use and it will thus be configured according to the inside volume of the mask. If an internal volume of air trapped in the mask of the order of 150 ml is considered, the quantity of water necessary for its saturation at a temperature of 50° C. is 0.0125 g, starting from completely dry air. Thus, the quantity of water required is small. However, a greater quantity of water must nevertheless be carried to enable proper control of the evaporation during the use of the mask. Tests have shown that by using a quantity of water less than 0.5 g, it was difficult to control the evaporation throughout the application of the mask, which lasts approximately ten minutes, such that the part forming a reservoir may become entirely empty and dry at the end of the application time, which is not desirable for an optimum result.

In the example embodiment represented, the mask comprises 510 orifices 32 having an average diameter of 1.30 provided in a wall of average thickness comprised between 1.10 and 2.15 mm.

Considering furthermore that the maximum quantity of water to carry is essentially limited by the quantity of energy necessary for its evaporation, it is possible to employ a member forming a reservoir able to carry appreciably more water than the mass of 0.5 g envisioned, for example up to 1.5 g, for an internal volume of the mask in use of the order of 150 ml.

It has moreover been found that a member forming a reservoir such as described with reference to the appended drawings, and comprising orifices 32 enabling the storage of a maximum of 1.5 g of water, when said member forming a reservoir is manipulated slowly and without jolting, can retain between 0.7 g and 1 g water when it is manipulated without any special precaution, or slightly drip-dried, which corresponds to an ideal quantity of water (or of liquid) to carry for a mask having an internal volume of the order of 150 ml.

Concerning the energy to provide during the use of the mask for the evaporation of the water and the saturation of the air present in the mask, it may be considered that three quarters of the energy provided leaves as heat losses to the surroundings. Considering that 0.5 g of water must be evaporated, ten minutes of heating at approximately 8 Watts provides 4.8 kJ, which is approximately four times the energy necessary for the evaporation of 0.5 g of water. This compensates for the anticipated losses.

Of course, according to the quantity of water to evaporate, which depends on the quantity of air maintained inside the mask, the required energy may be approximated in similar manner, and consequently adapted. In practice, temperature regulation is carried out, so as to maintain the air contained in the mask at a suitable temperature or within a range of suitable temperatures, for example comprised between 35° C. and 50° C. and preferably comprised between 38° C. and 48° C., throughout the application of the mask. The internal vapour/air temperature a few millimetres in front of the cornea is ideally approximately 40° C. during the treatment. The efficacy of treatment depends not only on the vapour/air temperature, but also on the level of saturation and movement of the air inside the system (movement of the vapour/air mixture).

The temperature regulation may be obtained by a regulation of the power of the supply for the heating means 14. The regulation of the power may consist in applying a suitable power, or in the cyclical activation and turning off of the heating means 14 over time. Furthermore, the heating power is limited, independently of the regulation, for reasons of the safety of the user (for example in order to avoid any burn risk).

The removable member 2 is conformed to surround the eyes of the user. In particular, the wall 31 of the removable member 2 may be conformed to extend substantially orthogonally relative to the face of the user wearing the mask. The removable member 2 may have an outside shape, at least over a portion, matching part of the inside shape of the main body 1, so as to be able to be received therein and linked by matching of shape or insertion fitting. The portion having such matching of shape is preferably the portion of the wall 31 comprising the orifices 32. This portion of the removable member 2 comprising the orifices 32 corresponds to a portion 33 that is distal relative to the face of a user wearing the mask.

The first part 3 of the removable member 2 may be made from plastic material, which is preferably sufficiently rigid to provide good stability of the first part, that is to say little deformation when the mask is applied to the face of a user.

In the example represented here, the orifices 32 are distributed over the wall 31, such that the liquid can be stored in a way that is distributed around the user's eyes. In particular, the orifices 32 may be distributed in four groups of orifices over the wall 31, i.e. an upper group in the top part of the removable member 2, a lower group in the bottom part of the removable member 2, a first lateral group situated on a right lateral portion (i.e. the right of the user wearing the mask) of the removable member 2 and a second lateral group situated on a left lateral portion (i.e. the left of the user wearing the mask) of the removable member 2.

The distribution of the orifices around the user's eyes has several advantages. This configuration increases the clearance in front of the user's eyes, allowing the user to blink when he uses the masks. Blinking enhances the effect of saturated hot air regarding the unblocking the meibomian glands.

Because the wall of the mask situated in front of the user's eyes is not used as reservoir, this wall may be dedicated to other functions. For example, a transparent wall may maintain clear vision during the use of the mask.

Furthermore, the heating means are distributed on the periphery of the inside surface of the main body 1, to heat the liquid contained in the orifices 32 by heat conduction. This configuration of the mask, as well as the position of the battery in the upper zone of the frame 11 reduces the cantilevered weight of the mask (in other words, most of the weight of the mask is at the vicinity of the user's face when the mask is used). This improves the comfort of use of the mask.

A distribution into several groups, for example into four groups of orifices as described above, for example enables orifices to be produced by groups, on manufacture of the removable member 2. Typically, the orifices of a same group may be oriented in line with axes that are parallel to each other. The orientation corresponds to the general direction of extension of the orifice, that is to say for example the main axis of the cylinder if the orifice has a substantially cylindrical shape.

In the case of the four groups defined above, the orifices of the upper and lower groups able to be oriented in a first direction and the orifices of the lateral groups may be oriented in a second direction.

The first and second directions may be at a right angle to each other.

In the case of orifices 32 obtained on moulding the first part 3, the orientation of the orifices is defined by the cylindrical pins passing through the volume of the mild. In an industrial context, these pins are parallel to each other for a same group of orifices. The groups of orifices may be separated by solid zones 38, which facilitate the putting in place of the tooling on moulding the first part 3, without degrading too much the distribution in the mask of the water to evaporate.

As the direction of the orifices is not necessarily strictly perpendicular to the wall 31 for all the orifices, the orifices 32 may have slightly different shapes, defined, for a round orifice, by the intersection of a straight cylinder oriented according to the main axis of the orifice and the complex shape of the wall 31.

As illustrated in FIGS. 2 and 3, the first part 3 has, in addition to the orifices 32 conjointly forming a reservoir, other notable functional members. The orifices 32 must be positioned facing or against the heating means 14 of the main body 1 when the removable member 2 is linked to the main body, while said heating means 14 must be disposed at a sufficient distance from the skin and eyes of the user for the heat generated by the heating means 14 for the evaporation of the liquid not to be unpleasant on use of the mask. Thus, the first part 3 comprises openings 35 of large size in its portion that is closest to the user's face, referred to as proximal portion 34 in relation to the user's face. It is generally the portion in the vicinity of the join between the first part 3 and the second part 4.

The openings 35 advantageously have dimensions as large as possible while enabling the first part 3 to maintain sufficient strength properties not to be easily damaged or crushed (deformed) on use of the mask. In other words, strips of material 36, sufficient to provide those strength properties, are kept.

The openings 35 may advantageously have a larger and smaller area (respectively corresponding to the lower and upper surfaces of the strips of material 36) having an angle oriented towards the inside space of the removable member (defined by the wall 31) and the mask, so as to bring liquid towards that inside space which could condense in that zone during the application of the mask.

The wall 31 of the first part 3 may also comprise an aperture 37, dimensioned and positioned such that said wall 31 of the first part 3 does not mask the temperature sensor (or sensors) comprised by the main body 1 when the removable member 2 is linked to said main body, in order for said temperature sensor to measure a temperature inside the mask as best possible. The measurement of the temperature at one or more points of the inside space of the mask enables regulation of the power of the heating means 14 during the use of the mask.

The sealing function of the removable member 2 concerns the sealing of the removable member 2 in relation to the user's face, and thus more generally of the mask in relation to the user's face. The sealing function of the removable member also concerns the sealing of the removable member 2 relative to the main body 1, in order to form in the mask a sealed inside volume in which the air saturated with vapour of a liquid (generally water) is maintained in front of the user's eyes during the application of the mask. By sealing, it should thus be understood that air-tightness is created, that is sufficient to maintain a sufficient quantity of air in the inside volume of the mask without significant leakage to the ambient atmosphere. The system may in particular be dimensioned to compensate for a leakage of air which would generate a temperature drop of 2° C. (or less) of the air contained in the mask.

In order to ensure the sealing, the second part 4 of the removable member 2 may be produced from flexible material, which is preferably elastic. An elastomer (for example rubber-based or silicone based) may be employed.

As regards the sealing in relation to the user's face, this is obtained by contact of the second part 4 with the user's skin. The contact is formed substantially along a closed line or strip surrounding the user's eyes. To obtain good contact with the skin, the second elastic part 4 may deform to adapt to the shape of the user's face. Of course, in order to adapt perfectly to as many users as possible, the shape of the second part 4 may be adapted according to the morphology of the face or to the age of the user. Thus, it is possible to create removable members having different shapes as regards the second part 4, or more generally a zone intended for the contact with the face, in order for the user to be able to choose and use the removable member 2 which is the best adapted to the shape of her face.

The second part 4 may be the only part of the masks which contacts the user's face. The removable member 2 may be changed not only to best comply with the shape of the face of the user, but also for hygiene issues.

Indeed, patients may have treatment on the medical professional's premises or possibly borrow/hire the device. This is a problem as there is a risk, particularly with individuals having a compromised tear film and sometimes an infectious condition, of passing their condition on to subsequent users. Attempts are made by device suppliers to clean and decontaminate the device between users. The effectiveness of this is unknown and it would in any case be inconsistent and inconvenient. A mask is very difficult to effectively decontaminate between users. Being made of multiple parts with internal electrical circuits etc., it cannot be autoclaved, or dipped in sterilising solution.

There is also a perceived patient resistance to using a second-hand device for what is an intimate personal therapy. There is a further perceived resistance particularly from professionals to offer a device that has already been used by someone else.

The removable member 2 may be changed between each user. Alternatively, the removable member, which has a simple construction (e.g. with a first part 3 made of solid plastics and a second part 4 made from flexible material), may be conveniently decontaminated using autoclave decontamination or a sterilising liquid.

Concerning the sealing in relation to the main body 1, the sealing is provided in the example represented here by the second part 4 of the removable member 2. In an embodiment not shown, a separate seal may be employed to provide this sealing.

Another advantage of the use of a two-part removable member 2 is that the rigid first part 2 gives the soft or flexible second part stiffness and acts as a former. The removable member 2 can be fitted into the mask for use in one easy motion without stretching an elastic part to fit the main body of the mask. This is of importance in regard to compliance, to ensure the device is used regularly as is required. At the start of the application of the mask, the orifices 32 together forming a reservoir are filled with liquid, for example water. The filling is for example achieved by immersion of the removable member (or at least of the part of the removable member 2 comprising orifices 32) in a container filled with liquid. The removable member 2 is linked to the main body.

Preferably, the removable member 2 is clipped to or has an insertion fit with the main body.

A further advantage of having a removable member 2 is that the mask may be configured not to be usable when a removable member 2 is not fitted into the main body 1. When the removable member is absent (and the main part of the main body 1 is not on a base as described hereafter), the heating means 14 may be disabled, and/or, the shape of the main body may be such that the mask cannot be worn without the removable member 2. This eliminates the possibility of using the device without the water carrier being fitted and enhances the safety of use and reliability of the mask.

The main body may have been pre-heated, preferably by an external energy source, before putting the removable member in place, such that the electrical supply of the heating means 14 by a battery 15, during the application of the mask, only serve for keeping the air in the mask at a desired temperature, for example in a temperature range going from 38° C. to 48° C. In this case, the use of the battery just for maintaining the temperature enables batteries to be used of smaller size and weight than if the battery also served for the heating, which improves the comfort of the apparatus for the user when the mask is worn. Pre-heating without the removable member 2 being fitted into the main body avoids liquid evaporation before the mask is placed on the user's face.

The user then positions the mask on her face. The inside spade of the mask is rapidly saturated with vapour (for example water) coming from the orifices 32 forming a reservoir.

The optimal time of application is of the order of ten minutes. This time enables the secretions accumulated by the meibomian glands to be rendered fluid, and the start of their decongestion. The decongestion may advantageously be improved by a massage of the eyelids after the application of the mask.

Figure 4:
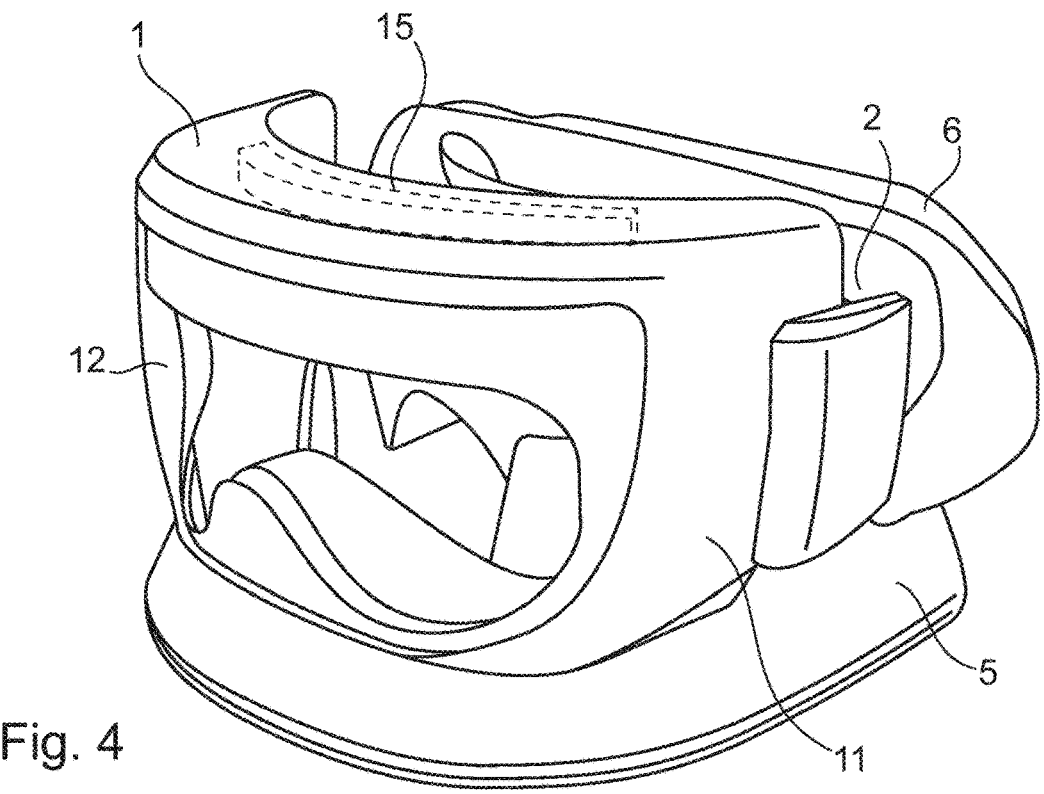
FIG. 4 presents a diagram, in a view in three dimensions, of a set in accordance with an embodiment of the invention the mask of FIG. 1 and a base.
Figure 5:
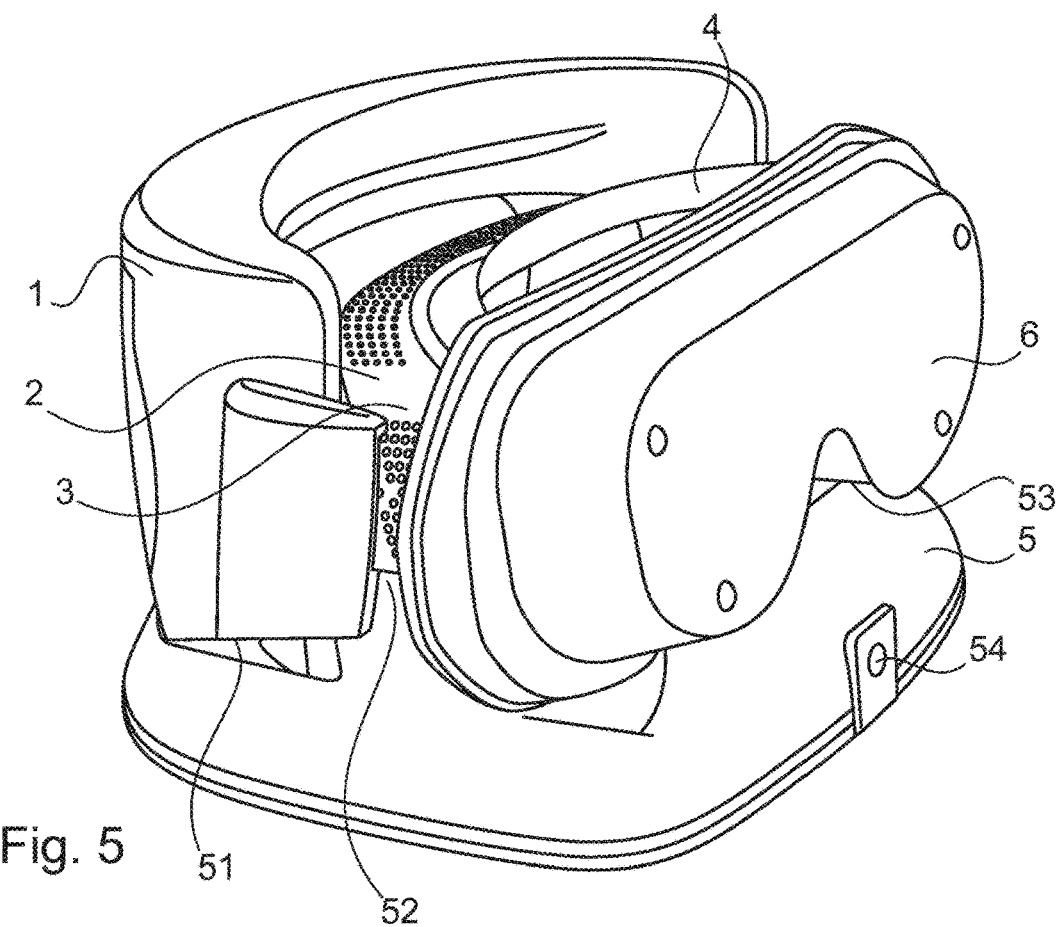
FIG. 5 presents a diagrammatic view in three dimensions of the set of FIG. 4, the base receiving in particular the members constituting the mask.

FIGS. 4 and 5 present two views of a set to which the invention also relates, comprising a mask as described above and a base 5.

The base 5 provides a support for the mask when it is not used. In particular, the base 5 is advantageously formed to receive the main body without the removable member. The base 5 for example has a hollow 51 of shape substantially matching an inside shape of the main body 1, but not making it possible to be accommodated therein when the removable member 2 is linked to the main body 1.

The base 5 may comprise a housing 52 configured to receive the removable member 2.

The base 5 may also comprise a reception means 53 for a receptacle 6, which is adapted for the filling with liquid of the orifices 32 of the removable member 2.

The receptacle 6 has a sufficient depth to immerse the orifices 32 of the removable member 2. The shape of the receptacle is such that it has a cavity of shape similar to that of the wall 31 of the removable member 2, in order to limit the quantity of liquid necessary for the filling of the receptacle.

As it is configured to receive the mask, as two members, as well as the receptacle 6, the base enables the members constituting a set according to the invention (mask comprising the main body 1 and the removable member 2, base 5 and receptacle 6), to be centralized, in particular when the device is stored between uses.

The base 5 enables the electrical supply of the main body to be provided. For this, the base 5 may comprise a plug 54 for its connection to an electrical network, where appropriate via a suitable transformer. The electrical supply of the base enables the battery of the main body 1 to be recharged. This recharging may be carried out via electrical contacts in the hollow 51, the main body comprising corresponding contacts. The recharging may, in another variant of the invention, be performed by induction. In the case of recharging via electrical contacts, the system may for example be configured in order for the recharging of the battery to be performed in a time ranging from 30 minutes to 1 hour.

The electrical supply of the base may also enable the heating means 14 of the main body to be directly supplied (that is to say without employing the battery 15 in order to improve the life thereof). This is possible when the supply of the main body by the base is provided by means of physical contacts. This enables the heating means to be brought to temperature before use of the mask, which enables the use of a battery of lower capacity, and a fast temperature rise. Indeed, the temperature rise necessitates a large quantity of energy, delivered at high power in order for said temperature rise to be fast. Such power could not be delivered by a battery carried in the mask of a volume and mass acceptable for autonomous use.

For example, the pre-heating may be carried out with a power of the order of 18 Watts, which makes it possible by way of example to attain the desired temperature in 3 to 5 minutes starting from an ambient temperature of the order of 20° C. After the desired temperature in the mask has been attained, the supply power of the heating means is reduced (for example to approximately 6 Watts) in order to maintain the temperature of the mask while waiting for a user to extract it from the base 5. Optionally, the temperature maintenance may be programmed for an amount of time corresponding to the time available to the user to come to extract the mask and carry out her treatment. When that time has elapsed the heating power is cut to avoid abusive or undesired energy consumption and optimize the life of the heating means.

Thus, the set comprising the base 5, the mask, and the receptacle 6 may be used in the following sequence.

The receptacle 6 is separated from the reception means 53, and filled with liquid, for example water. The removable member 2 is withdrawn from the housing 52, and soaked in the liquid contained in the receptacle, such that the orifices 32 of the removable member 2 are filled with the liquid. The removable member 2 is extracted from the receptacle. The main body of the mask may possibly be pre-heated on the base 5 by activation, for example prior to the steps already described, of its heating means.

The pre-heating has several advantages. It makes it possible in particular to efficiently compensate for the drop in temperature induced by the filling of the removable member by means of a cold liquid, for example water, the removable member being then linked to the pre-heated main body. The pre-heating enables a fast temperature rise of the mask on application, optimizing the therapeutic effect for the pre-defined time of application, by virtue of a fast heat transfer in the desired zone.

The removable member 2, of which the members are filled with water, may optionally be slightly drip-dried above the receptacle 6, to eliminate possible excess liquid. The removable member 2 is lined to the main body 1.

The user then positions the mask on her face, for a predefined time of application, during which the heating power is set to compensate for the drop in temperature induced by the wearing of the mask, and in particular the drop in temperature induced by the filling of the removable member by means of a cold liquid, for example water, and which is linked to the preheated main. For example, the compensation may be made by virtue of a power of the order of 9 Watts by means of the battery that is carried.

The heating power may also be regulated to ensure the maintenance of temperature during the treatment by virtue of a power of the order of for example 5 to 6 Watts.

When the application time has elapsed, there may be an electronic beeper that gives an intermittent reminder to place the device back on the base 5 after application. The base makes it possible to recharge and dry the main body 1 and the removable member 2. Preferably, it is only on the base that the device can be started for its next operation cycle.

After elapse of the application time, the mask is removed from the user's face. The latter may manually perform a massage of her eyes in order to improve the unblocking of the meibomian glands. The majority of the water present in the orifices of the removable member has generally been evaporated during the application. The removable member 2 is withdrawn and may optionally be cleaned for example by soaking in a cleaning solution and thereby limiting microbial development. The main body 1 is repositioned on its base in the hollow 51. An optional phase of actuation of the heating means may then be carried out, in order to dry the main body of possible remaining liquid which may have been deposited or formed thereon during the application of the mask. This limits or avoids possible microbial development on the mask.

The removable member 2 may be stored on the base 5 in the housing 52, possibly after wiping and possibly be dried thereon. Once the receptacle 6 has been emptied and possibly dried, it may also be stored on the base 5, on the reception means 53.

The base and/or the mask are provided with electronic devices for the management of the charging of the battery of the mask and possibly of the pre-heating of the heating means. The mask is provided with electronic devices enabling the application to be managed. In particular, means may enable the duration of application of the mask to be timed and to indicate (by an audible and/or visible signal) the elapse of the desired duration of application. In some variants, this application duration may be controlled. A control of the length of application or treatment time may enable the life of the heating means to be optimized.

The operating times and temperatures may be set on manufacture but may optionally be programmable. In particular, the device may optionally be re-programmable, for example to adapt the application duration and the temperature during the application according to the user, and to be able to change the duration and temperature if need be. The re-programming of the device may be carried out via a wireless or wired communication system. For example, a dedicated application (installed on an external system such as a computer, a tablet, a smartphone or a dedicated re-programming unit) enables the selection of the length of application time and of the temperature or temperature range for regulation in the mask. The external system communicates, for example via a wireless link (for example Bluetooth (registered trademark)) with the mask for its re-programming.

The mask (in particular the main body 1 of the mask) may comprise one or more light-emitting indicators, for example light-emitting diode based, which can be seen from the outside and/or from the inside (that is to say by a user wearing the mask). The light-emitting indicators may enable a variety of information to be communicated to the user: the charge level of the battery, the fact that a charge is in course, the on or off status of the device, the activation of the heating means, the elapse of the desired application time, etc.

The mask (in particular the main body of the mask) and/or the base 5 may be a so-called connected object. More particularly they may be adapted to communicate, via wired or wireless communication means and protocol with an external system. The base may comprise a communication port. The mask and/or the station can receive or send data to an electronic device or to a server. The electronic device may be a personal electronic device such has a computer, a smartphone or a tablet, which executes a dedicated program or application. The data sent or received may relate to information on use of the mask, maintenance, etc.

The connection may be used for example to indicate to a practitioner how often the patient has used the mask per day, per week, per month, and so follow up the use on each of his appointments with the doctor. This connection system could also indicate the temperature recorded at the beginning and end of treatment, for example.

The mask or the base may be remotely programmable, e.g. with respect to the application time, the heating temperature or profile of temperature during application.

In some embodiments, a communication may also be established between the main body of the mask and the base. This makes it possible for the mask and the base to exchange information. For example, a programming of the mask may be carried out by providing data to the base which transmits said data to the mask. Data stored in the mask during use may be downloaded via the base.

The invention so developed provides an autonomous mask enabling dry eye to be acted against by improving the quality of the tear film covering the cornea of the eye, by subjecting the meibomian glands to hot air, typically saturated with water vapour, for a desired time of application. The mask described in the invention is autonomous in that it comprises the heating means enabling the water to be vaporized for the time of application of the mask, as well as the energy source, i.e. an electric battery, enabling the heating means to be supplied at least so as to maintain a desired temperature in the mask for the time of application. Furthermore, the particular configuration of the reservoir for liquid (generally water) employing orifices retaining the water under the effect of the surface tension between the water and the wall of these orifices enables precise control of the quantity of water carried in the mask at the start of application as well as easy filling and cleaning

The invention claimed is:

1. An eye mask configured to cover the eyes and the eyelids of a user, the eye mask comprising:
   a main body comprising an electrical heater and a battery configured to supply the electrical heater; and
   a removable member removably linked to the main body, said removable member comprising
   a first part comprising a wall forming a reservoir provided with retaining orifices configured to retain a liquid, under the effect of surface tension between said liquid and walls of the retaining orifices, the wall forming the reservoir being configured to surround the eyes of the user wearing said mask, and
   a second part providing air-tightness with the face of the user wearing the mask.

2. The mask according to claim 1, wherein the first part and the second part are constituted by distinct pieces, the first part being constituted of a material that is plastic, and the second part being formed of a material that is elastic.

3. The mask according to claim 2, wherein the removable member is air-tight with respect to an inside wall of the main body to form a volume in front of the eyes of the user, the volume being that is sealed to the air.

4. The mask according to claim 1, wherein the removable member is air-tight with respect to an inside wall of the main body to form a volume in front of the eyes of the user, the volume being sealed to the air.

5. The mask according to claim 4, wherein the second part of the removable member further provides air-tightness with respect to the inside wall of the main body.

6. The mask according to claim 1, wherein the retaining orifices are configured in terms of size and number to retain between 0.5 grams and 1.5 grams of water.

7. The mask according to claim 1, wherein, when the removable member is linked to the main body, the wall forming the reservoir is in contact with an inside surface of the main body, the electrical heater being configured so as to heat said inside surface.

8. The mask according to claim 7, wherein the removable member is linked to the main body by matching of shape between the inside surface of the main body and an outside surface of the wall forming the reservoir.

9. The mask according to claim 1, further comprising:
a temperature sensor; and
a regulation system configured to regulate the supply of the electrical heater by the battery, the temperature sensor and the regulation system being linked.

10. A set comprising:
the mask according to claim 1; and
a base configured to receive the main body of said mask and supply the main body of the mask with electricity to recharge the battery thereof.

11. The set according to claim 10, wherein the set is configured such that the electricity supplied to said main body enables the heating of the electrical heater without the electrical heater being supplied by the battery, when said main body is received on the base.

12. The set according to claim 11, wherein the main body of the mask or the base comprises a wired or wireless communication system configured to communicate with a remote system.

13. The set according to claim 10, wherein the base comprises a hollow configured to receive the main body of the mask, said hollow having a shape preventing the main body of the mask from being received on said base when the removable member is linked to said main body.

14. The set according to claim 10, wherein the base comprises a housing configured to receive the removable member.

15. The set according to claim 10, further comprising a receptacle configured to receive the removable member for filling said wall forming the reservoir, the base further comprising a receiver configured to receive the receptacle when said receptacle is empty.

16. The mask according to claim 1, wherein the retaining orifices are configured in terms of size and number to retain between 0.7 grams and 1 gram of water.

17. A method of using the mask according to claim 1, the method comprising:
filling the retaining orifices of the wall with liquid;
linking the removable member to the main body;
supplying the electrical heater by the battery; and
regulating the supply of the electrical heater for the entire or part of a time of application, in order to maintain the air contained in an internal space of the mask within a predefined temperature range for the whole or the part of the time of application.

* * * * *